United States Patent
Swords et al.

(10) Patent No.: US 9,402,968 B2
(45) Date of Patent: Aug. 2, 2016

(54) COLORECTAL DELIVERY DEVICE

(71) Applicant: Mercy Medical Research Institute, Inc., Springfield, MO (US)

(72) Inventors: Robert L. Swords, Springfield, MO (US); Roger Huckfeldt, Nixa, MO (US); Jesse Taylor, Springfield, MO (US); Martin Reuter, Flemington, MO (US)

( * ) Notice: Subject to any disclaimer, the term of this patent is extended or adjusted under 35 U.S.C. 154(b) by 72 days.

(21) Appl. No.: 13/939,932

(22) Filed: Jul. 11, 2013

(65) Prior Publication Data

US 2014/0018775 A1 Jan. 16, 2014

Related U.S. Application Data

(60) Provisional application No. 61/670,452, filed on Jul. 11, 2012.

(51) Int. Cl.
A61M 31/00 (2006.01)
A61M 11/00 (2006.01)

(52) U.S. Cl.
CPC .............. *A61M 11/00* (2013.01); *A61M 31/00* (2013.01); *A61M 2210/1067* (2013.01)

(58) Field of Classification Search
USPC ................... 604/26, 264, 275, 328, 507, 514
See application file for complete search history.

(56) References Cited

U.S. PATENT DOCUMENTS

| 3,266,674 | A | * | 8/1966 | Martin ................ B65D 83/72 141/3 |
| 4,874,363 | A | * | 10/1989 | Abell ............................ 604/28 |
| 5,352,437 | A |   | 10/1994 | Nakagawa et al. |
| 5,447,496 | A | * | 9/1995 | Bove et al. ................... 604/514 |
| 5,759,520 | A |   | 6/1998 | Sachetto |
| 5,972,310 | A |   | 10/1999 | Sachetto |
| 6,046,179 | A |   | 4/2000 | Murch et al. |
| 6,166,024 | A |   | 12/2000 | Sandborn |
| 6,468,245 | B2 | * | 10/2002 | Alexandersen ............. 604/105 |
| 7,141,237 | B2 |   | 11/2006 | Abram et al. |
| 7,341,741 | B1 |   | 3/2008 | Sachetto et al. |
| 7,704,518 | B2 |   | 4/2010 | Tamarkin et al. |
| 8,070,736 | B2 | * | 12/2011 | Nishtala et al. ............. 604/328 |
| 8,617,100 | B2 | * | 12/2013 | Eini et al. ...................... 604/73 |
| 8,926,577 | B2 | * | 1/2015 | Nishtala et al. ............. 604/328 |
| 2004/0011364 | A1 |   | 1/2004 | Dhuper et al. |
| 2004/0161447 | A1 | * | 8/2004 | Paul ............................ 424/430 |
| 2009/0205658 | A1 |   | 8/2009 | Tanaka et al. |
| 2010/0130426 | A1 |   | 5/2010 | Young et al. |
| 2010/0166672 | A1 |   | 7/2010 | Boutignon et al. |
| 2010/0174252 | A1 | * | 7/2010 | Tanghoej et al. ............ 604/328 |
| 2010/0249752 | A1 |   | 9/2010 | Tanghoej |

FOREIGN PATENT DOCUMENTS

WO 2011158232 A2 12/2011

OTHER PUBLICATIONS

International Search Report and Written Opinion issued in PCT/US2013/050097, Oct. 15, 2013, 12 pages.

* cited by examiner

*Primary Examiner* — Nathan R Price
*Assistant Examiner* — Morgan Lee
(74) *Attorney, Agent, or Firm* — Michael A. Williamson; Polsinelli PC (57) ABSTRACT

The colorectal delivery device provides a device for rectal delivery of therapeutic compositions to the colon of a patient. The composition may be a foam application in some embodiments. The device allows medical personnel to add therapeutic drugs to the pressurized canister immediately prior to administration to the patient.

14 Claims, 13 Drawing Sheets

COLORECTAL DELIVERY DEVICE

RELATED APPLICATION

This application claims the benefit of U.S. patent application Ser. No. 61/670,452 filed Jul. 11, 2012, the disclosure of which is incorporated herein by reference.

BACKGROUND

Field of the Invention

The colorectal delivery device is in the field of medical devices. More specifically, it is in the field of drug delivery devices for delivering pharmaceutical and therapeutic drugs to the colon of a patient by means of the rectum. In some embodiments, the pharmaceutical and therapeutic drugs described herein are delivered as part of a composition that foams during delivery to the patient's colon.

SUMMARY OF THE INVENTION

A colorectal delivery device comprises a canister for containing the drug in a liquid solution and a propellant; a nozzle assembly connected to the canister for dispensing the drug from the canister; and a delivery assembly connected to the nozzle assembly; wherein the liquid solution and propellant are dispensed from the canister through the nozzle assembly to the delivery assembly.

In embodiments, the colorectal delivery device further comprises a drug delivery port for injecting the drug into the canister. In other embodiments, the delivery assembly comprises a cannula, a quick connect fitting and a retention cuff; wherein the quick connect fitting is attached to the first end of the cannula, and the retention cuff is disposed around the cannula between the midpoint of the length of the cannula and the second end of the cannula.

In further embodiments, the nozzle assembly comprises a valve, an aerator and a quick connect fitting; wherein the valve is attached to the canister for dispensing the liquid solution and the propellant, and the aerator is connected to the valve for causing the liquid solution to foam upon delivery to the colon.

DETAILED DESCRIPTION

The colorectal delivery device provides an improved capability for delivering a therapeutic agent such as pharmaceuticals or therapeutic drugs to the colon of a patient. The device allows medical personnel to load one or more drugs into the device immediately prior to delivery to the patient, for optimum flexibility and efficacy. It delivers the drug to the patient's colon as a foam with preferable treatment profiles as compared to a liquid delivery vehicle.

The device is suitable for treatment of colon infections, inflammatory bowel disease, clostridium difficile colitis, diverticulitis, and hyperkalemia, among other conditions. The drugs administered by the device may include, but are not limited to, antibiotics, metronidazole, vancomycin, mesalamine, corticosteroids including prednisone and solumedrol among others, steroids, and any drug or composition suitable for administration by foam in the colon. The device may also be used to administer an enema.

Figure 1A:
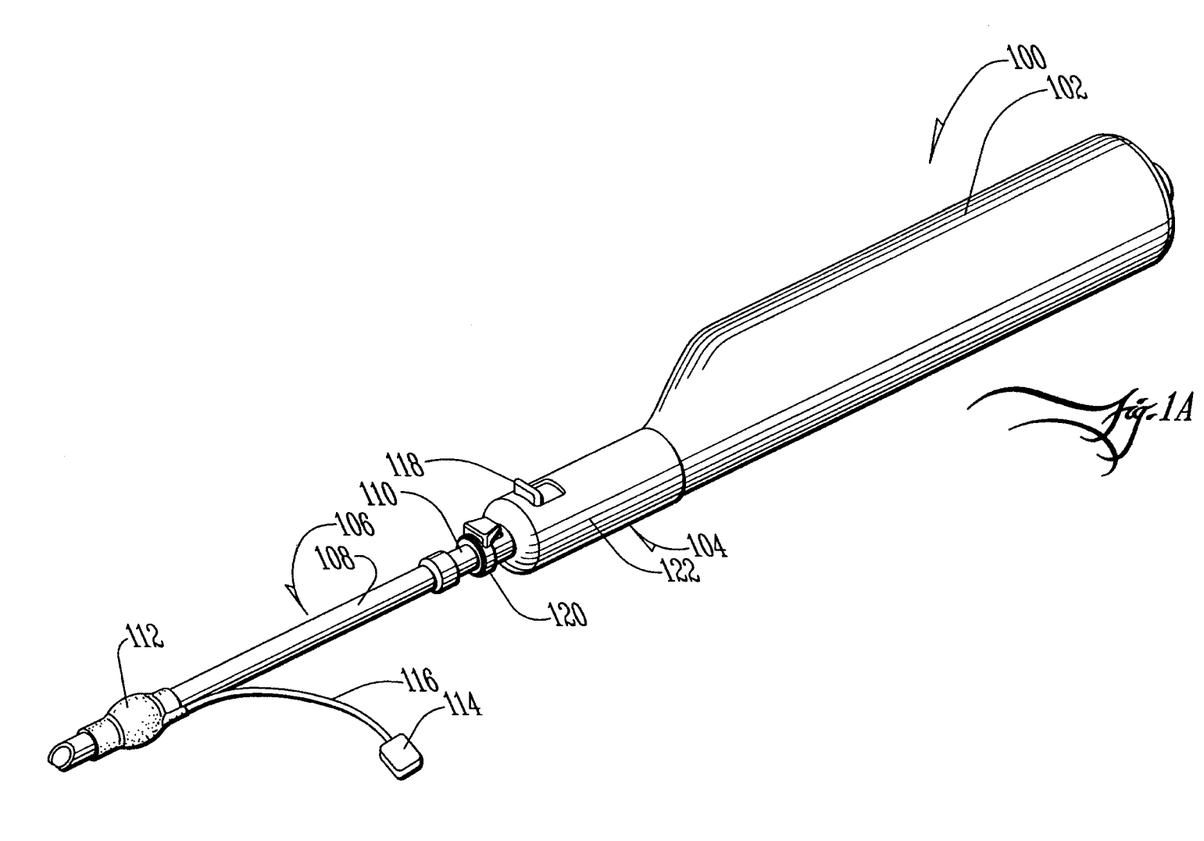
FIG. 1A is a perspective view of an embodiment of the colorectal delivery device.
Figure 1B:
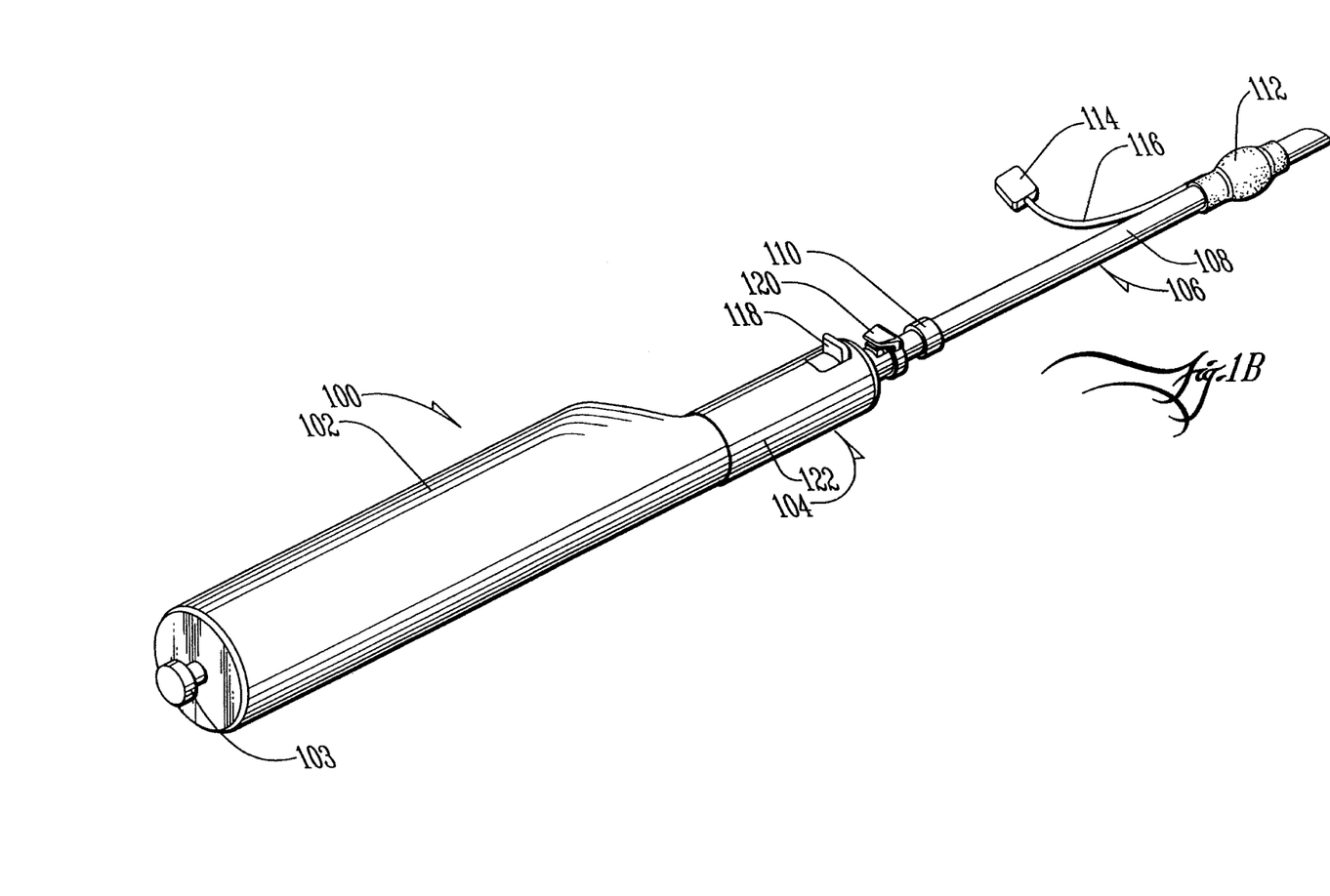
FIG. 1B is a perspective view of an embodiment of the colorectal delivery device.

Referring now to FIG. 1A and 1B, perspective views of an embodiment of the colorectal delivery device are depicted. The device 100 comprises a canister 102, a nozzle assembly 104, and a delivery assembly 106. The delivery assembly 106 provides a means for delivering pharmaceutical or therapeutic drugs in the canister 102 into the colon of a patient through the patient's rectum. In some embodiments, the canister 102 may be shaped eccentrically to allow for improved mixing of the propellant and the pharmaceutical or therapeutic drugs in the canister 102 when the canister is disposed in certain orientations. The various components of the device 100 may be sterilized during manufacture or by the medical personnel prior to use.

In a preferred embodiment, canister 102 contains a propellant and a therapeutic compound described in more detail below. The canister 102 may be preloaded with a therapeutic compound that includes the therapeutic agent, such as a pharmaceutical or therapeutic drug, or it may have only medically-inactive foaming components preloaded during manufacture. In a preferred embodiment, the canister contains water, typically purified medical grade USP water, a surfactant to promote formation of foam upon dispensing of the product, and compressed propellant gas. In a preferred embodiment the components of the composition, including the propellant gas, are all in the same chamber of the canister 102. In other embodiments, the composition may be divided into multiple chambers within canister 102 or within one or more flexible bags in the canister.

In typical embodiments, the canister 102 is pressurized between 15 and 25 p.s.i.g. with carbon dioxide. The canister is typically formed from metal or polymer material and must be resistant to corrosion by the surfactant, propellant or pharmaceutical or therapeutic drugs used in the composition. In preferred embodiments, the canister has a sufficient volume to contain (i) up to 100 mL of a solution of USP grade purified water and Betain (surfactant), and (ii) approximately 25 mL of a solution of water and pharmaceutical or therapeutic drug, with sufficient headspace or ullage to allow the production of 500-700 mL of foam product with a gas to liquid ratio of 5:1. In a preferred embodiment, the Betain/water/pharmaceutical solution has a Betain concentration of ten percent.

The medical personnel utilizing the device 100 may load pharmaceutical or therapeutic drugs into the canister through drug delivery port 103. In a preferred embodiment of the device, the delivery port is an opening in the canister covered by a septum that may be secured in place by a cap or lid with a hole allowing access to the septum.

The septum is preferably formed from a material that may be pierced by a needle for the introduction of a liquid into the canister 102 without releasing the pressurized contents of the canister 102. After the drug is introduced into the canister 102 through the needle and septum, the needle may be withdrawn from the septum and the septum will effectively seal the hole made by the needle as it is withdrawn. A removable cap may be provided to cover the delivery port 103 when not in use.

In other embodiments of the device, the drug delivery port 103 may comprise a one-way check valve for attaching to a drug source via a quick disconnect fitting, a Leur type connection for a syringe, or other similar suitable means for connecting a drug source to the device. The one-way check valve is oriented to allow material from the syringe or other attached source of drugs to be introduced into the canister 102 without allowing the contents of the canister 102 to escape.

The delivery assembly 106 may comprise a rectal catheter, a cannula or other similar means of delivering a composition into a person's colon through the rectum. In a preferred embodiment of the colorectal delivery device, the delivery assembly 106 comprises a rectal catheter that is formed from a cannula 108, or tube, with a quick connect fitting 110 on a first end of the tube and a retention cuff 112 around the cannula 108 and disposed between the second end of the cannula 108 and the midpoint of the cannula 108. In a preferred embodiment the quick connect fittings accept 7 mm inner diameter tubing, though other fitting and tubing sizes may be utilized in various embodiments of the device. In a preferred embodiment the delivery assembly 106 is approximately 12 inches in length.

The retention cuff 112 may comprise a balloon that expands around the cannula 108 to contact the inner surface of the patient's rectum. The retention cuff or balloon 112 is inflated after insertion of the catheter to prevent the foaming composition from exiting the colon through the rectum prematurely. The retention cuff 112 is provided with some means of inflation such as pump 114 and tube 116, whereby the medical personnel may inflate the balloon 112 after it has been properly positioned in the rectum of the patient. In some applications of the device, the retention cuff 112 is positioned superior to the internal anal sphincter prior to inflation. In some embodiments, pump 114 is a syringe either permanently or removable attached to tube 116 for pumping a measured volume of air into retention cuff 112.

Nozzle assembly 104 controls the flow of material from the canister 102 to the delivery assembly 106. Nozzle assembly 104 provides a convenient grip by which a user may hold the delivery device 100 and an actuator 118 for controlling the dispensing of material from the device 100. In the depicted embodiment, the actuator 118 is a sliding actuator whereby the user slides the actuator toward the canister 102 causing the nozzle assembly 104 to dispense material from the canister 102 through delivery assembly 106. When the user releases the actuator it returns to its original position and nozzle assembly 104 terminates the dispensing of material from the canister 102. In other embodiments of the nozzle assembly other types of actuators may be utilized, including but not limited to, buttons, triggers, switches, or other means of actuating a mechanism such as the nozzle assembly 104.

In embodiments the actuator may be provided with a safety guard to prevent accidental discharge of the device. In a preferred embodiment the safety guard comprises a removable cover or guard for the actuator 118. In other embodiments the safety guard may comprise a fixed guard over the actuator or a removable actuator 118 which may be removed from assembly 104 when not in use.

Figure 1C:
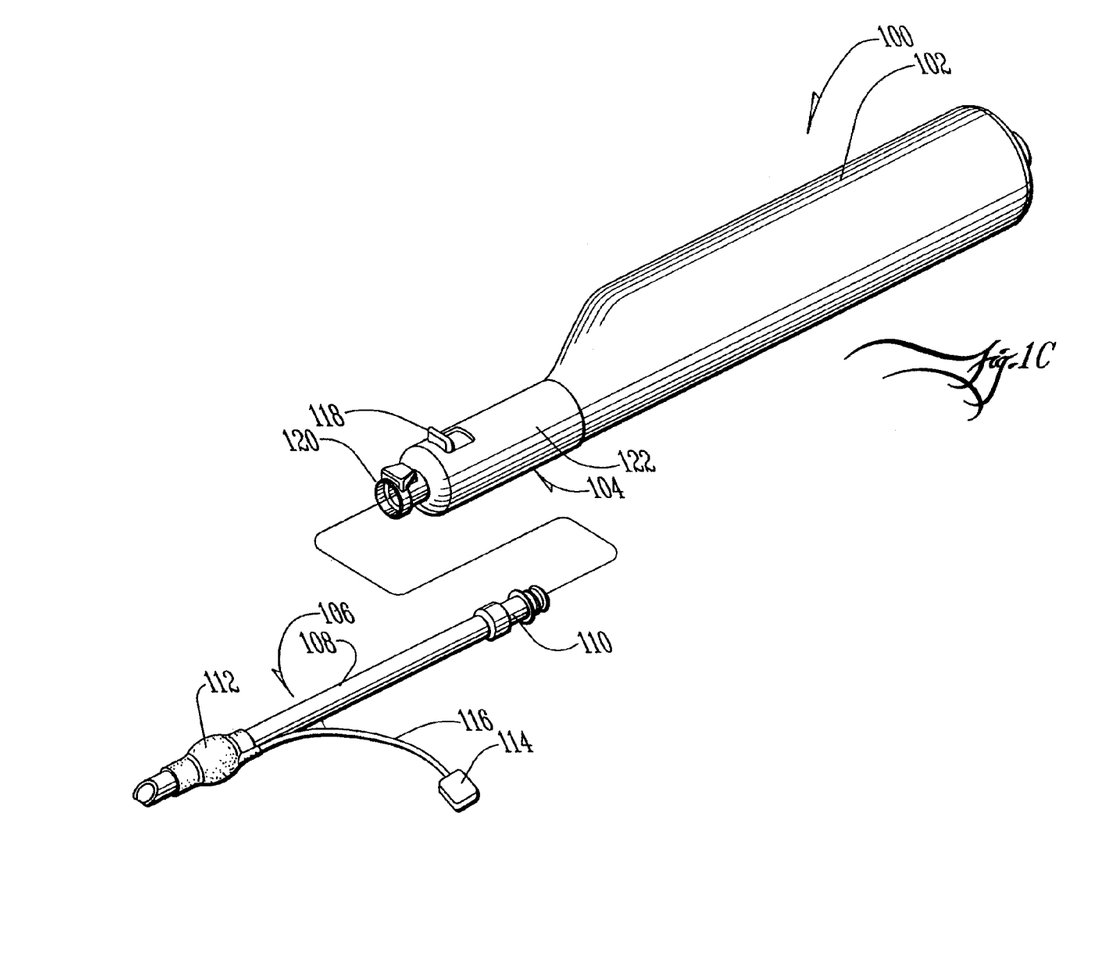
FIG. 1C is a perspective view of an embodiment of the colorectal delivery device.

Referring now to FIG. 1C, the device 100 is depicted with the delivery assembly 106 disconnected from the nozzle assembly 104. Quick connect coupling 120 on nozzle assembly 104 provides for the rapid connection and disconnection of the delivery assembly 106 from the nozzle assembly 104.

Figure 2A:
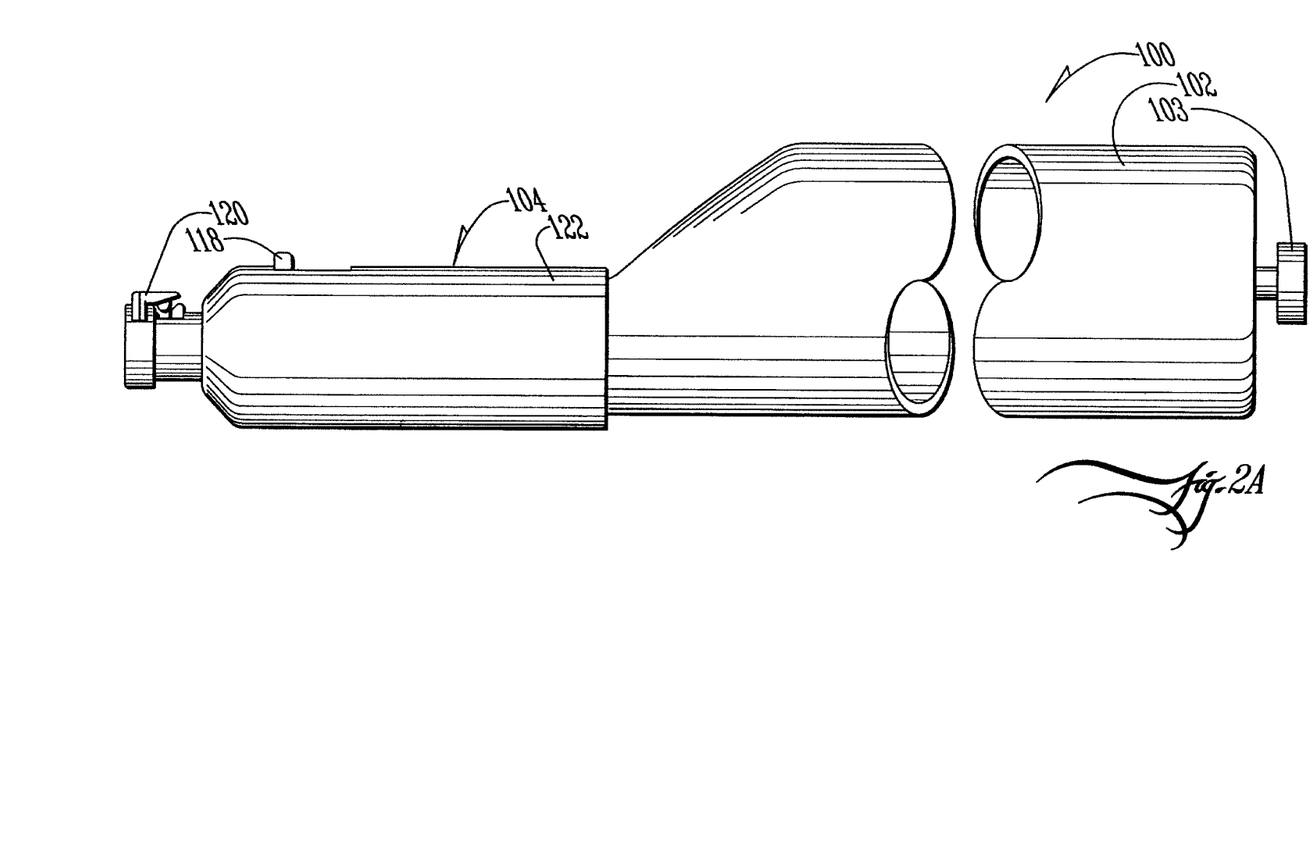
FIG. 2A is a side view of an embodiment of the colorectal delivery device.
Figure 2B:
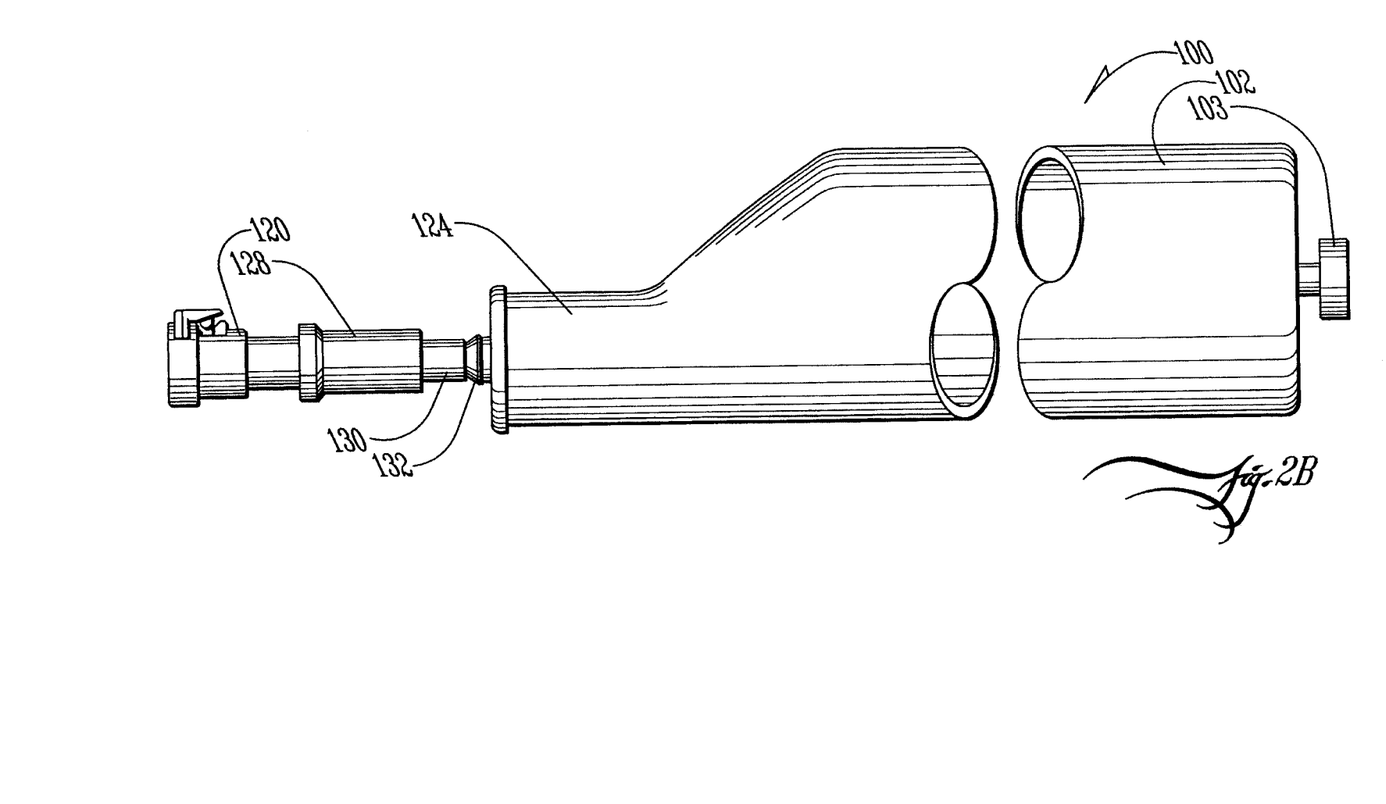
FIG. 2B is a side view of an embodiment of the colorectal delivery device.

Referring now to FIGS. 2A and 2B, side views of a portion of the colorectal delivery device 100 are depicted. Nozzle assembly 104 includes a nozzle assembly cover 122 which protects the internal components of the nozzle assembly 104, and provides a hand grip for the user of the device 100. In FIG. 2B, the nozzle assembly 104 is depicted without the cover 122 and the internal components of the nozzle assembly 104 can be seen extending from the neck region 124 of canister 102.

Figure 3A:
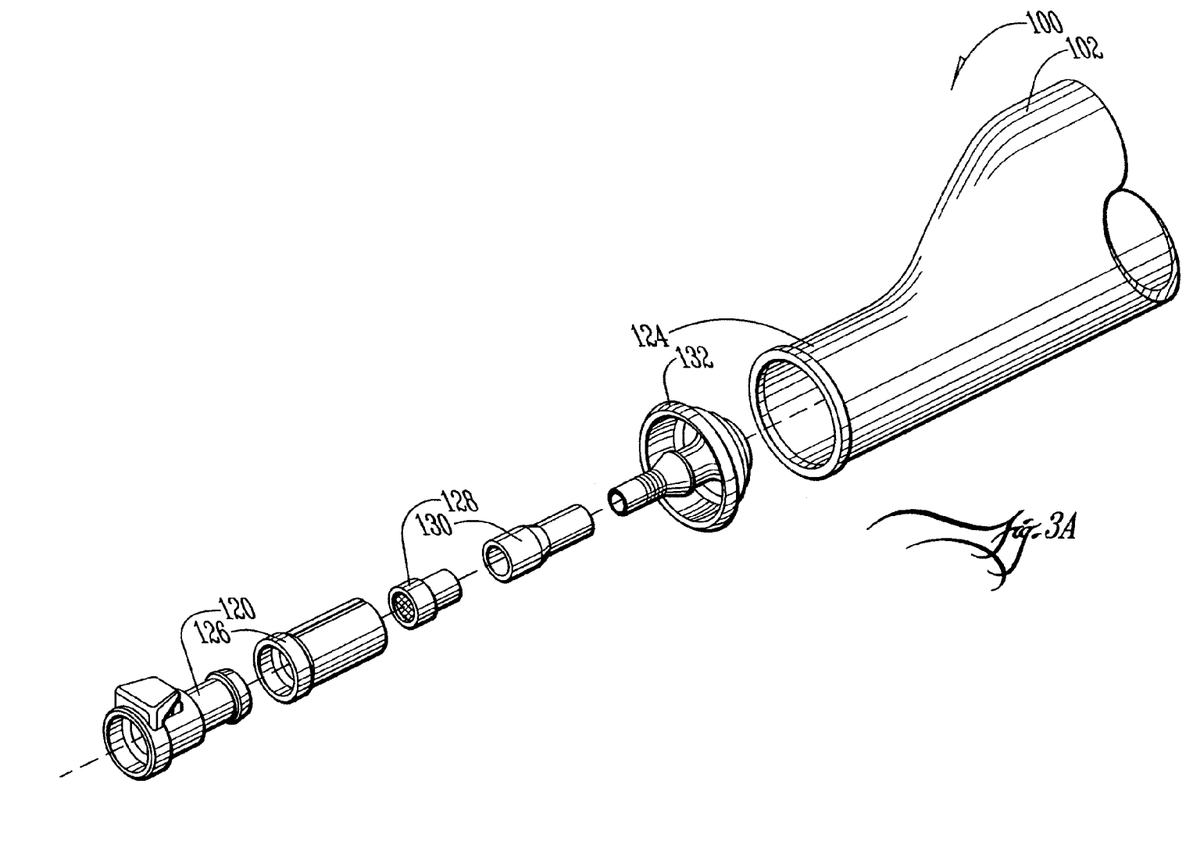
FIG. 3A is an exploded perspective view of a portion of an embodiment of the colorectal delivery device.
Figure 3B:
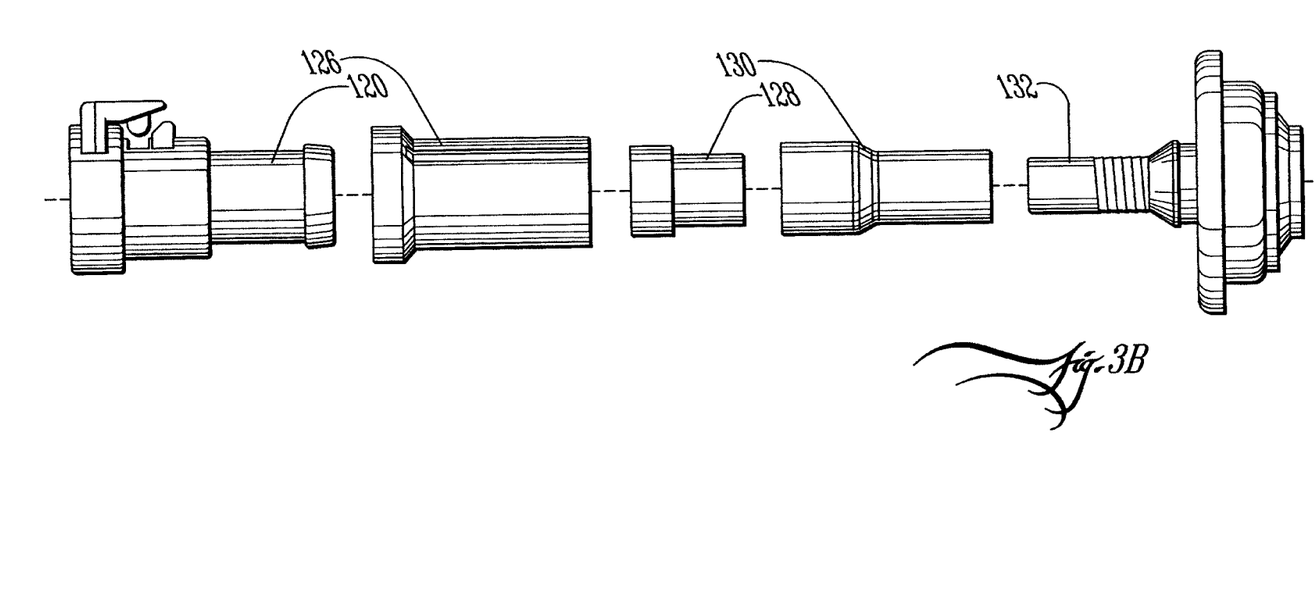
FIG. 3B is an exploded view of a portion of an embodiment of the colorectal delivery device.

Referring now to FIGS. 3A and 3B, exploded views of the nozzle assembly 104 are depicted, in perspective and plan view, respectively. Nozzle assembly 104 is provided with quick connect coupling 120 as described above, for releaseably connecting to the quick connect fitting 110 on delivery assembly 106. The quick connect coupling 120 is provided with a quick connect coupling on a first end thereof and a tubing connection flange on the second end thereof, and is substantially hollow to allow the passage of material through the coupling. The second end of quick connect fitting 120 connects to a first end of sleeve or tubing 126, typically by the insertion of the tubing connection flange into the inside of sleeve 126. The sleeve 126 may be formed with varying inner and outer diameters of tubing as necessary to accommodate the other components of the nozzle assembly 104.

Sleeve 126 is connected on a second end thereof to an aerator 128, or alternatively, aerator 128 may be disposed within sleeve 126 or may replace sleeve 126. The aerator is a typical aerator known for use in causing pressurized components to foam upon expulsion through the aerator. In a preferred embodiment of the device, the aerator is a double screen mesh aerator, though in embodiments other aerator devices may be utilized. In some embodiments of the system, a foaming composition may be utilized that does not require a mechanical aerator and in those embodiments, the system may not include an aerator. An example of a foaming composition that does not require a mechanical aerator is a self-foaming formulation of Octoxynol-9, xanthum gum and water.

If provided, the aerator is connected to valve 132 on canister 102 by sleeve or tubing 130. The aerator 128 may be partially disposed within sleeve 130, and sleeve 130 may extend partially inside sleeve 126. The actual configuration and interconnection of parts in the nozzle assembly 104 may vary in embodiments of the device 100. In a preferred embodiment of the device 100, the valve has an equivalent orifice of 0.023 $in^2$. Other orifice sizes may be utilized to accommodate necessary flow rates for various applications, and to allow horizontal operation of the device 100.

Figures 5A, 5B, 5C:
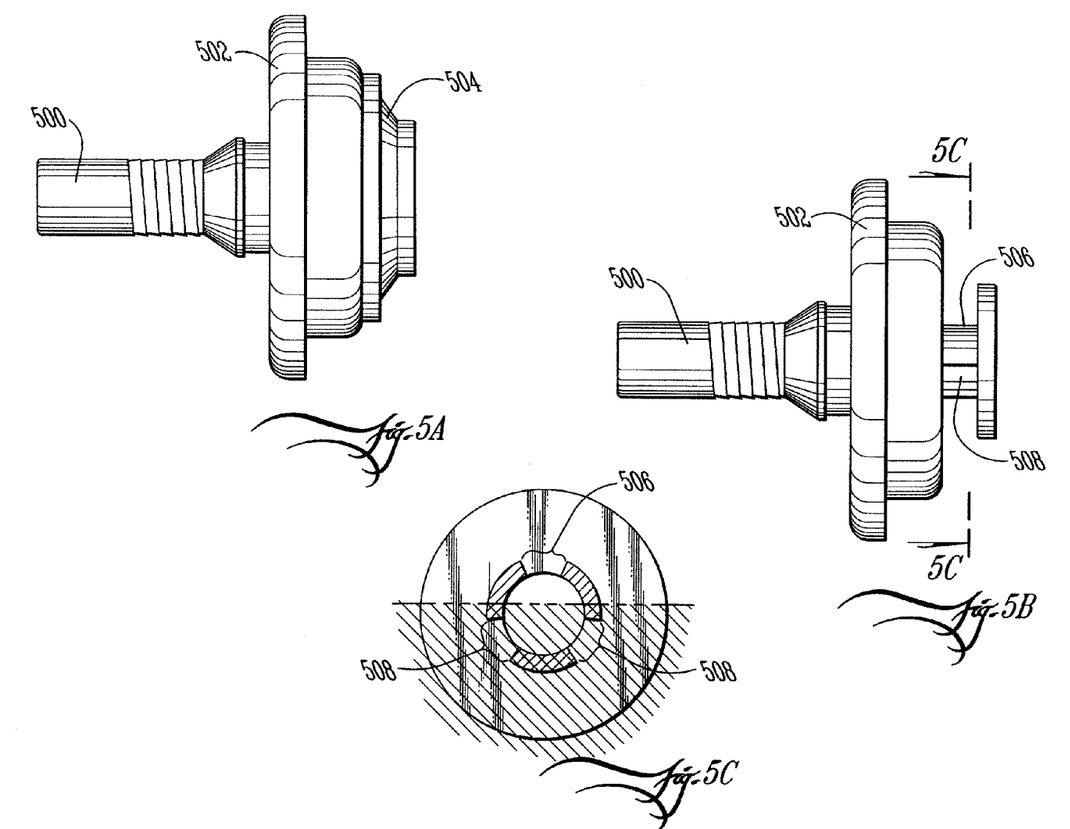
FIG. 5A is a side plan view of a portion of an embodiment of the colorectal delivery device.
FIG. 5B is a side plan view of a portion of an embodiment of the colorectal delivery device.
FIG. 5C is a plan view of a portion of an embodiment of the colorectal delivery device.

The valve 132 is attached to canister 102 to cover the end of neck 124 and seal the interior volume of the canister 102. The valve may be of any design that is susceptible for use with foaming aerosol products. A preferred embodiment of the valve is described with reference to FIG. 5 below.

Figure 4:
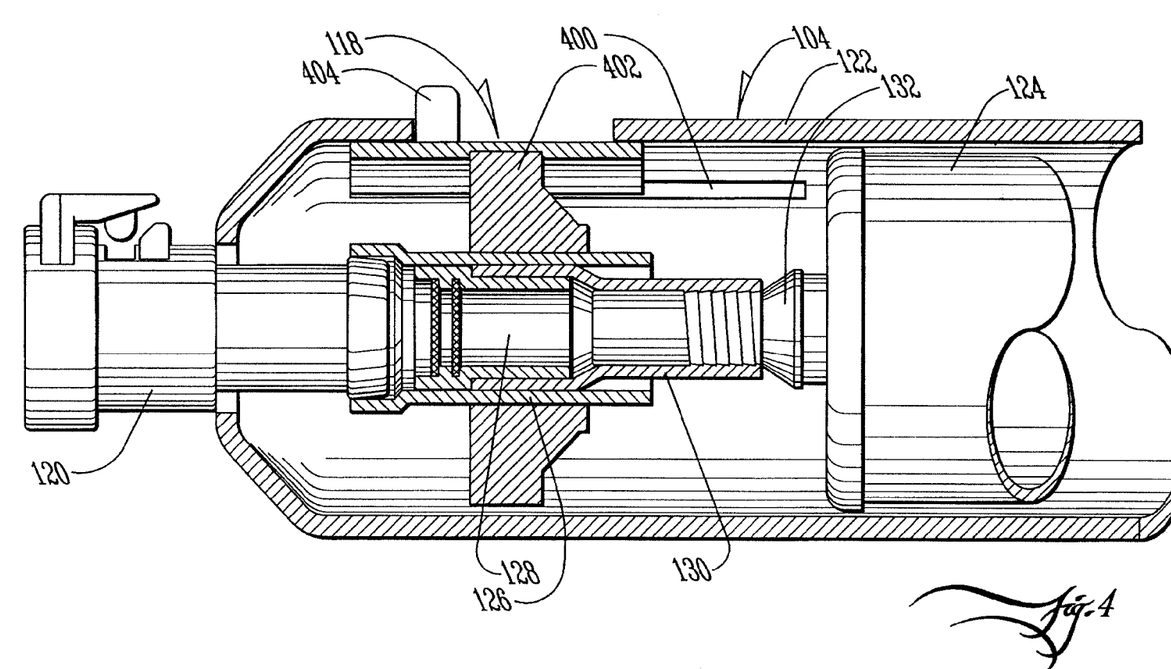
FIG. 4 is a cross-sectional detail view of a portion of an embodiment of the colorectal delivery device.

Referring now to FIG. 4, a cross-sectional view of the nozzle assembly 104 is depicted. The nozzle assembly cover 122 covers and protects the valve 132 and other components of the nozzle assembly 104 that deliver the contents of the canister to the cannula 108 of the delivery assembly 106. The nozzle assembly cover 122 in the depicted embodiment comprises a cylindrical tube, though in other embodiments the cover 122 may be square, polygonal, elliptical or asymmetrical in cross-section. The specific cross-section or design of the cover 122 in the depicted embodiments are not limiting of the colorectal delivery device.

The cover 122 is open on a first end thereof for connecting to the canister 102. The embodiment of the device 100 depicted in these figures has a canister 102 with a neck region 124 that fits within the open first end of the nozzle assembly cover 122. In other embodiments, the canister 102 may not have a neck region, there may be no overlap of the canister 102 and the cover 122, and canister 102 may connect to cover 122 in any method known for attaching such components. In a preferred embodiment, the nozzle assembly cover 122 is removable from canister 102 however it may be permanently attached thereto in other embodiments. The second end of the tube of cover 122 may be narrowed or formed to closely conform to the quick connect coupling 120 or other component of nozzle assembly 104.

The actuator 118 is depicted in an embodiment that slides back and forth within an aperture in cover 122. The actuator is disposed on rails or grooves 400 which slidably retain the actuator 118 in cover 122. The actuator is provided with an actuator collar that fits within cover 122 and engages sleeve 126 or some other component of the nozzle assembly 104. The actuator 118 is also provided with a flange 404 for a user to engage with thumb or finger to actuate the device 100. In other embodiments of the device, the actuator may function differently and still be within the scope of the invention.

When a user engages flange 404 and slides it toward the canister 102, the collar 402 presses sleeve 126 toward valve 132. When valve 132 is depressed, it opens and allows material from canister 102 to be dispensed through the nozzle assembly. When the user releases pressure on flange 404, the valve 132 will return to the closed position and the flow of material through nozzle assembly 104 will stop.

In the embodiment depicted in FIG. 4, the coupling 120 mates with the sleeve 126. The aerator 128 is disposed therein and sleeve 130 is disposed partially within sleeve 126 and around a portion of aerator 128. Sleeve 130 also connects to the stem of valve 132. The combination of components provides a channel for dispensing product from the canister 102 and forming a foam composition during delivery to a patient. Other combinations of components may be utilized in the nozzle assembly 104 within the scope of the invention. The components 120, 126, 128 and 130 may be glued together, provided with barbed friction fittings, or otherwise secured together in a manner appropriate to the materials used for the components.

Referring now to FIGS. 5A, 5B and 5C, a preferred embodiment of the valve 132 is depicted, though other valves may be utilized in the device 100. In a preferred embodiment, the valve comprises a valve stem 500 with an internal channel for dispensing material through the valve 132. The stem 500 extends through valve body 502 and is connected to the body 502 by a flexible seal. The valve stein 500 extends through valve body 502 into the pressurized container 102. In embodiments, the valve stem 500 is biased by a spring or other mechanism to pull against valve body 502 and o-ring 504 to close the valve 132. In other embodiments, the valve stem 500 may be held in the closed position by the pressure of compressed gas in the canister 102. FIG. 5B depicts the valve with o-ring 504 removed. When valve stem 500 is depressed by a user, valve stem 500 exposes openings in the valve stem 500 or valve body 502, thus allowing the contents of the container 102 to escape through the channel in the valve stem 500. When the valve is released it returns to the closed position.

In the depicted embodiments of the canister 102, no dip tube is provided and the canister is intended to be held with its longitudinal axis in a substantially horizontal position. In other embodiments of the device, utilizing different valves or dip tubes for picking up the liquid composition, vertical orientations may be preferred. When held horizontally, the liquid in container 102 will form a level similar to that depicted in FIG. 5C across the inner face of valve body 502. The valve stem 500 is provided with three outlets, 506 and 508, to allow the contents of canister 102 to escape. When canister 102 is held horizontally, outlet 506 receives propellant and outlets 508 receive the liquid composition when the valve 132 is actuated. In varying applications, the shape of the canister 102 may be modified to maximize performance and propellant/liquid mixing when operated horizontally or at other angles. This may include asymmetrical or eccentric shapes for the container 102.

Figures 6A, 6B:
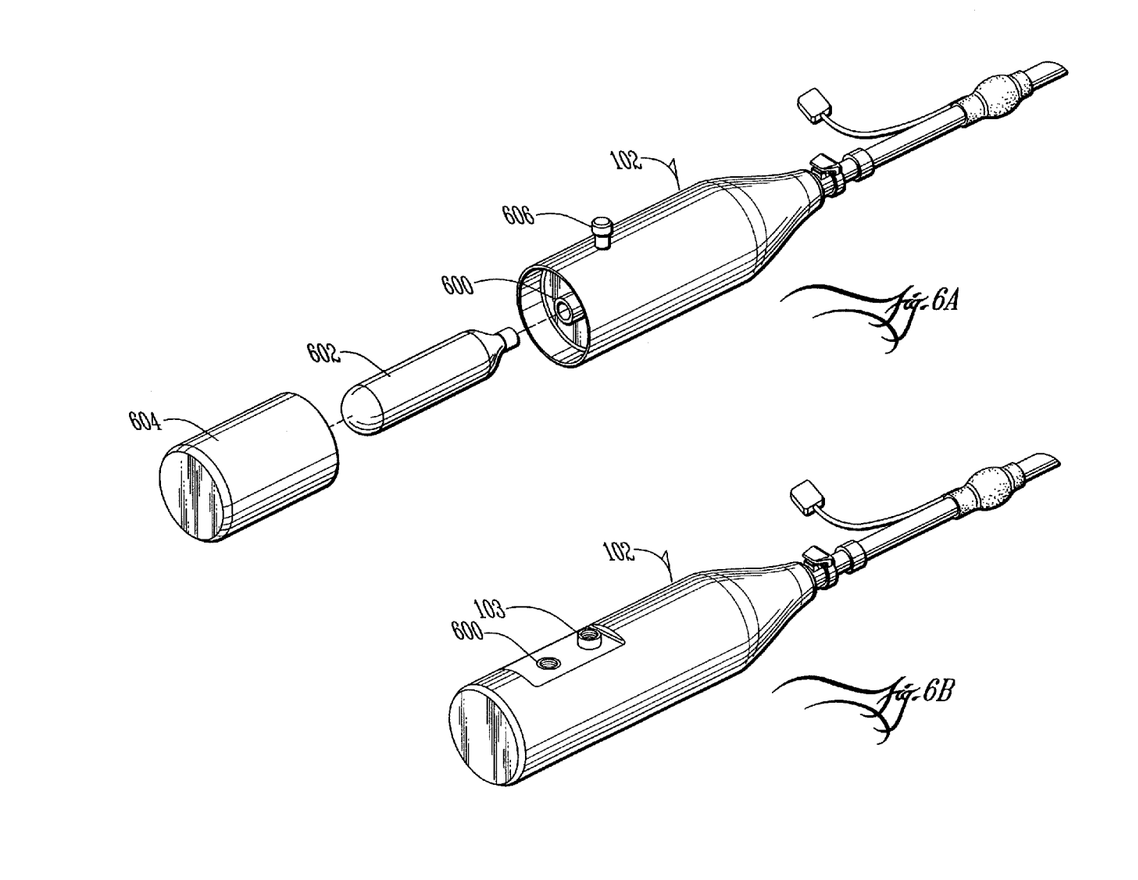
FIG. 6A is an exploded perspective view of an alternative embodiment of the colorectal delivery device.
FIG. 6B is a perspective view of an alternative embodiment of the colorectal delivery device.

In an alternative embodiment, a two canister system is provided, as depicted in FIG. 6A. In this alternative embodiment, the canister 102 is unpressurized and may be provided with a removable cap or a port such as the drug delivery port 103 depicted in previous figures and shown in FIG. 6B, for introducing a therapeutic compound into canister 102. In some embodiments, the canister 102 may be preloaded with the foaming formulation, but not with any pharmaceutical or therapeutic compound. The canister 102 in this alternative embodiment is also provided with a charging port 600 for receiving pressurized propellant from a second canister or propellant container 602 in preparation for use with a patient.

A user of this alternative embodiment first adds the desired pharmaceutical or therapeutic compound to the foaming formulation by injecting the compound through the drug delivery port or the removable cap, if necessary. The first canister 102 is resealed, and the contents of the canister may be shaken or otherwise agitated for improved mixing of the contents. Then the user attaches the second canister 602, containing pressurized propellant, to the charging port 600 and pressurizes the first canister 102 with the propellant. The second canister 602 may be a canister of pressurized carbon dioxide or compressed air, or any other suitable pressurized gas or liquefied propellant. A cover 604 may be provided to cover the second canister 602 by attaching to either canister 102 or 602. The device can then be used to administer the foam compound to the colon of the patient.

In an alternative embodiment of the system utilizing two canisters, a charging button 606 is provided for controlling the pressurization of the first canister 102. After attaching the second canister 602 to the first canister 102, medical personnel may actuate the charging button 606 to pressurize the first canister 102. In an alternative embodiment, the medical personnel actuate the charging button 606 for a predetermined period of time to charge the first canister 102 to the desired pressure. The appropriate charging time may vary depending on the pressure and volume of the two canisters.

Referring now to FIG. 6B, a perspective view of an alternative embodiment of the colorectal delivery device is depicted. The depicted embodiment has a charging port 600 located on the side of canister 102 and a drug deliver port or removable cap 103 for introducing therapeutic or pharmaceutical compounds into the canister 102. In other aspects, the embodiment in FIG. 6B operates similarly to the embodiment described above with respect to FIG. 6A.

Figures 7A, 7B:
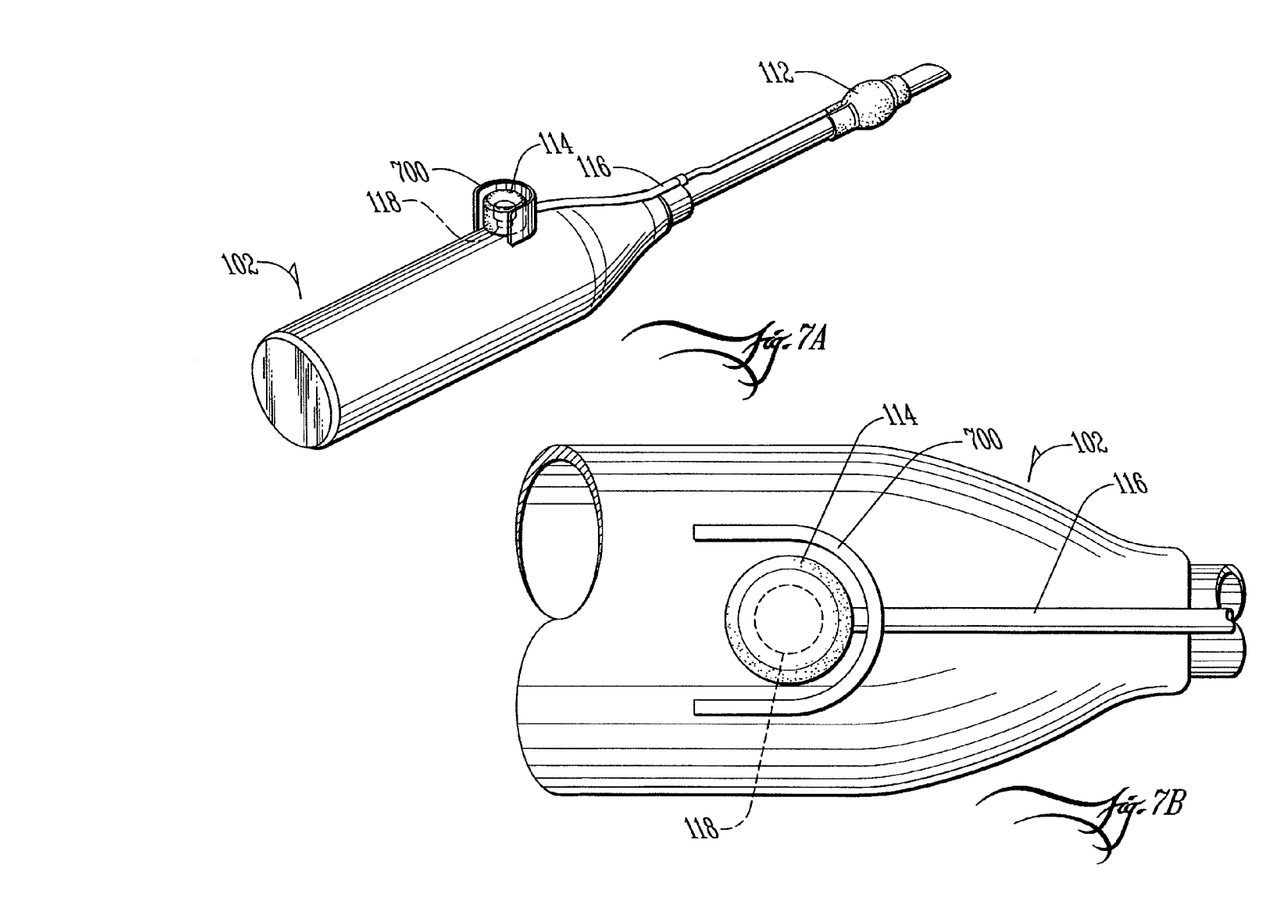
FIG. 7A is a perspective view of an alternative embodiment of the colorectal delivery device with a multi-stage actuator.
FIG. 7B is a top plan view of an alternative embodiment of the colorectal delivery device with a multi-stage actuator.

In a further alternative embodiment of the system, a multi-stage actuator is provided for inflating the retention cuff and dispensing the foam product sequentially. Referring now to FIG. 7A, the multi-stage actuator is depicted. In this embodiment, the actuator 114 for the retention cuff 112 is disposed on the outer surface of the canister 102 and above the actuator 118. In this embodiment, actuator 114 is an air bladder that, when depressed, forces air through line 116 into the retention cuff 112 thereby inflating the cuff. As the user depresses the actuator 114, the cuff 112 inflates, and when actuator 114 is depressed the user continues to depress actuator 118, which dispenses the contents of the canister 102 into the patient's colon. A protective shield 700 may be provided around all or a portion of the multi-stage actuator assembly to prevent accidental actuation of the device.

Figure 8A:
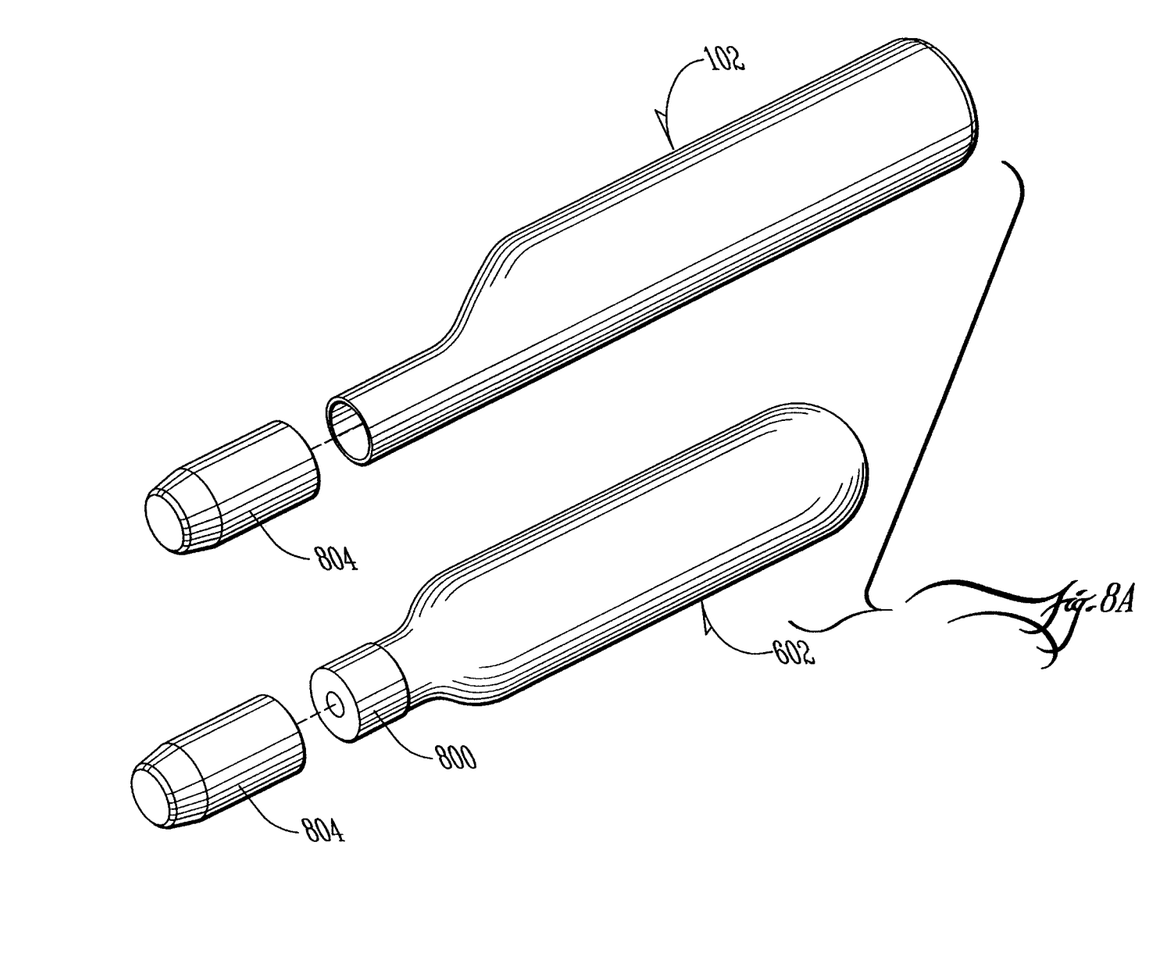
FIG. 8A is a perspective view of an alternative embodiment of the colorectal delivery device.

Referring now to FIG. 7B, a top plan view of an alternative embodiment of the colorectal delivery device with a multi-stage actuator is depicted. The actuator 118 is located underneath the center of actuator 114. Shield 700 surrounds three sides of actuator 118 with an opening on the remaining side to allow the user's thumb to actuate the device while the user holds canister 102 with the same hand Referring now to FIGS. 8A-8C, perspective views of an alternative embodiment of the colorectal delivery device utilizing a separate propellant canister are depicted. In FIG. 8A, the two canisters are depicted with the caps 804 thereof removed. Canister 102 is unpressurized and valve 132 has not been attached to the opening in canister 102. Canister 102 may be empty or may contain components of the foaming therapeutic compound. In this configuration a user may add therapeutic agents or other desired additives to the other contents of the canister 102. Propellant container 602 contains the propellant to be added to canister 102 before use thereof on a patient. Container 602 is provided with coupling port 800 to transfer propellant to canister 102 when appropriate.

Figures 8B, 8C:
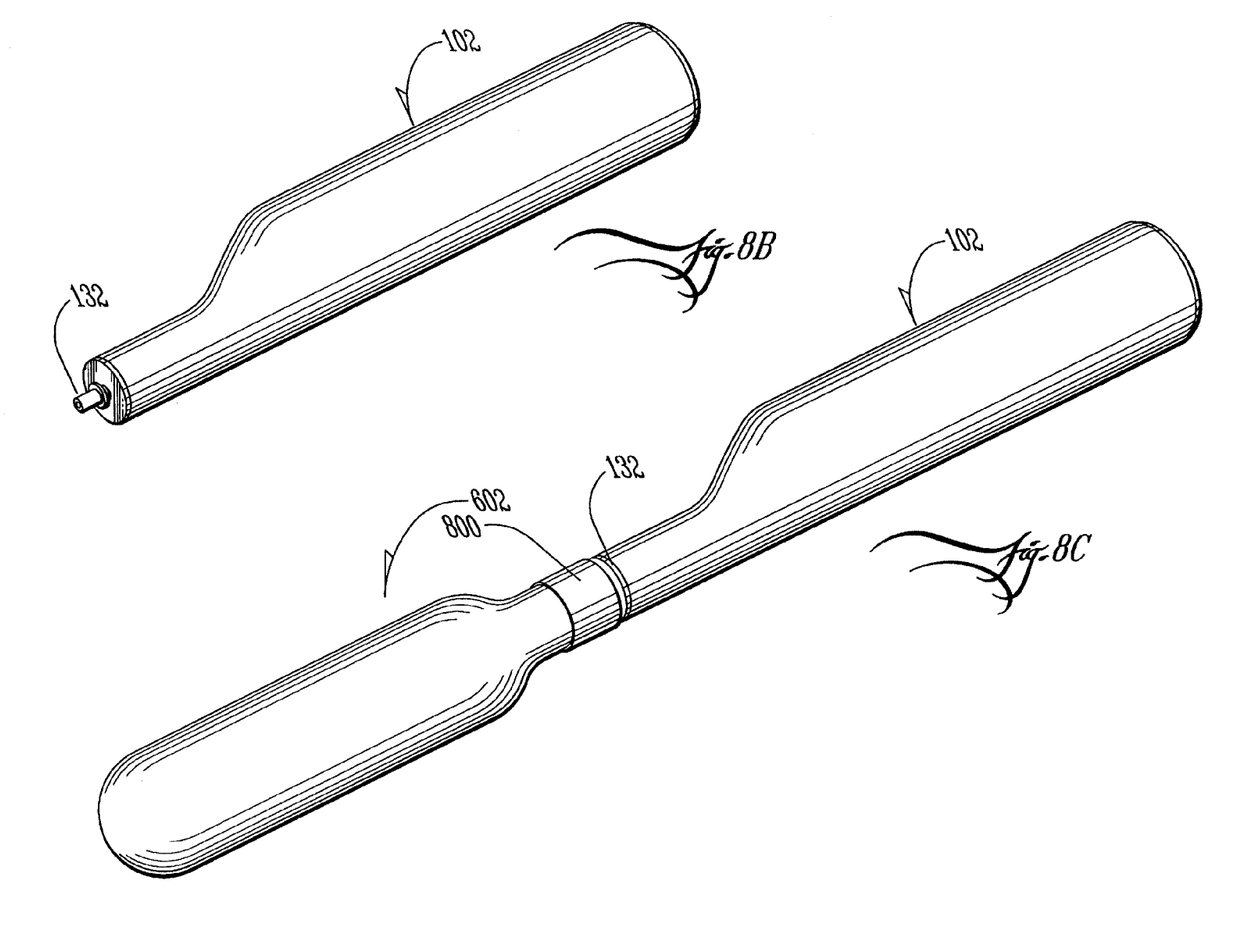
FIG. 8B is a perspective view of an alternative embodiment of the colorectal delivery device.
FIG. 8C is a perspective view of an alternative embodiment of the colorectal delivery device.

Referring now to FIG. 8B, in this embodiment of the device after a therapeutic agent has been added to the canister 102, valve 132 is affixed to canister 102 by threads, adhesive or other methods of attaching the valve to the canister. The canister 102 may then be agitated to mix the therapeutic agent with the other elements of the therapeutic compound in the canister.

As depicted in FIG. 8C, propellant container 602 is then coupled to canister 102 by attaching coupling port 800 to valve 132. The coupling port 800 is designed to open valve 132, and to allow the propellant in container 602 to pass through the valve 132 into container 102. This may involve pressurized gas from container 602 entering into canister 102 and pressurizing the contents thereof, or liquid propellant entering the canister 102 through valve 132. Other types of propellants may be used as appropriate for the application.

Once canister 102 has been charged with propellant from container 602, the coupling port 800 is detached and nozzle assembly 104 is attached to valve 132 as shown in FIGS. 1A-1C. Similarly, delivery assembly 106 is attached to nozzle assembly 104. The device is then ready for use to administer the therapeutic agent to the patient.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described.

What is claimed is:

1. A device for administering a therapeutic compound or a therapeutic agent to a colon of a patient comprising:
   a canister for containing a therapeutic compound or a therapeutic agent; and
   a nozzle assembly connected to the canister for dispensing a compound from the canister; and
   a delivery assembly for inserting into a colon of a patient connected to the nozzle assembly;
   said canister further comprises a port for adding the therapeutic compound or the therapeutic agent into the canister; wherein said port is separate from the nozzle assembly;
   said nozzle assembly incorporating an actuator for selectively releasing a propellant and the therapeutic compound or the therapeutic agent from the canister; and
   wherein the delivery assembly includes a pump and wherein the pump is incorporated into the nozzle assembly and the actuator is disposed within the pump.

2. The device of claim 1 wherein the delivery assembly comprises a cannula, a retention cuff, a pump pneumatically connected to the retention cuff by a tube; wherein the first end of the cannula is attached to the nozzle assembly; and wherein the retention cuff is disposed around the cannula between the midpoint of the length of the cannula and the second end of the cannula, and the retention cuff may be inflated by actuating the pump.

3. The device of claim 2 wherein the nozzle assembly comprises a valve and an aerator in fluidic communication with the valve; wherein the valve is attached to the canister, and the aerator is connected to the valve.

4. The device of claim 3 wherein the port comprises a removable cap for pouring the therapeutic agent or the therapeutic compound into the canister.

5. The device of claim 3 wherein the port comprises a septum through which the therapeutic agent or the therapeutic compound may be injected into the canister.

6. The device of claim 3 further comprising a therapeutic compound and a propellant disposed in the canister; the therapeutic compound comprising water, a surfactant, and a therapeutic agent.

7. The device of claim 3 further comprising a propellant container containing the propellant and a charging port in the canister for receiving the propellant from the propellant container.

8. The device of claim 7 further comprising a charging button on the canister or the propellant container for discharging the propellant from the propellant container to the canister.

9. The device of claim 3 wherein the canister has an asymmetric shape to allow the canister to be held in a horizontal configuration during administration.

10. A method of using the device of claim 1;
    the device further comprises a therapeutic compound and a propellant disposed in the canister;

the therapeutic compound comprising water, a surfactant, and a therapeutic agent;

said method comprising the steps of: inserting the cannula of the delivery assembly into the colon of the patient until the retention cuff is disposed within the rectum of the patient;

actuating the pump on the delivery assembly to inflate the retention cuff;

actuating the actuator on the nozzle assembly to dispense the therapeutic compound from the canister into the colon;

deflating the retention pump; and removing the cannula from the colon of the patient.

11. The method of claim 10 further comprising the step of injecting the therapeutic agent or the therapeutic compound into the canister through a port in the canister.

12. A method of using the device;

of claim 1 comprising the steps of: adding the therapeutic agent or the therapeutic compound to the canister through the port in the canister;

attaching the propellant container to the charging port in the canister; dispensing the propellant from the propellant container into the canister;

inserting the cannula into the colon of the patient until the retention cuff is disposed with the rectum of the patient;

actuating the pump on the delivery assembly to inflate the retention cuff; actuating the actuator on the nozzle assembly to dispense the therapeutic compound from the canister into the colon;

deflating the retention pump; and removing the cannula from the colon of the patient.

13. A device for administering a therapeutic agent to a colon of a patient comprising:

a canister for containing a therapeutic compound;

a nozzle assembly connected to the canister for dispensing a compound from the canister; and a delivery assembly for inserting into a colon of a patient connected to the nozzle assembly;

said nozzle assembly incorporating an actuator for selectively releasing a propellant and the therapeutic compound from the canister;

wherein the delivery assembly comprises a cannula, a retention cuff, a pump pneumatically connected to the retention cuff by a tube; wherein the first end of the cannula is attached to the nozzle assembly;

wherein the retention cuff is disposed around the cannula between the midpoint of the length of the cannula and the second end of the cannula, and the retention cuff may be inflated by actuating the pump; and wherein the pump is incorporated into the nozzle assembly and the actuator is disposed within the pump.

14. A method of using a device for administering a therapeutic agent to a colon of a patient; the device comprising:

a canister for containing a therapeutic compound; and a nozzle assembly connected to the canister for dispensing a compound from the canister; and a delivery assembly for inserting into a colon of a patient connected to the nozzle assembly; and said nozzle assembly incorporating an actuator for selectively releasing a propellant and the therapeutic compound from the canister;

wherein the delivery assembly comprises a cannula, a retention cuff, a pump pneumatically connected to the retention cuff by a tube;

wherein the first end of the cannula is attached to the nozzle assembly; and wherein the retention cuff is disposed around the cannula between the midpoint of the length of the cannula and the second end of the cannula, and the retention cuff may be inflated by actuating the pump;

wherein the nozzle assembly comprises a valve and an aerator in fluidic communication with the valve;

wherein the valve is attached to the canister, and the aerator is connected to the valve;

wherein the device further comprises a therapeutic compound and a propellant disposed in the canister;

the therapeutic compound comprising water, a surfactant, and a therapeutic agent;

said method comprising the steps of:

inserting the cannula of the delivery assembly into the colon of the patient until the retention cuff is disposed within the rectum of the patient;

actuating the pump on the delivery assembly to inflate the retention cuff;

actuating the actuator on the nozzle assembly to dispense the therapeutic compound from the canister into the colon;

deflating the retention pump; and removing the cannula from the colon of the patient.

* * * * *